United States Patent
Miyai

(10) Patent No.: US 9,683,926 B2
(45) Date of Patent: Jun. 20, 2017

(54) EXHAUST GAS SAMPLING APPARATUS AND EXHAUST GAS SAMPLING METHOD

(71) Applicant: HORIBA, Ltd., Kyoto (JP)

(72) Inventor: Masaru Miyai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 393 days.

(21) Appl. No.: 14/228,459

(22) Filed: Mar. 28, 2014

(65) Prior Publication Data

US 2014/0290336 A1    Oct. 2, 2014

(30) Foreign Application Priority Data

Mar. 29, 2013   (JP) .................................. 2013-073200

(51) Int. Cl.
   *G01N 19/10*   (2006.01)
   *G01N 1/22*    (2006.01)

(52) U.S. Cl.
   CPC ........... *G01N 19/10* (2013.01); *G01N 1/2252* (2013.01); *G01N 2001/2255* (2013.01)

(58) Field of Classification Search
   CPC ..................................................... G01N 19/10
   USPC ................................ 73/23.32, 29.01, 863.02
   See application file for complete search history.

(56) References Cited

U.S. PATENT DOCUMENTS

| 6,490,937 | B2* | 12/2002 | Hanashiro | G01N 1/2258 |
| | | | | 73/863.11 |
| 8,603,310 | B2* | 12/2013 | Ishida | G01N 27/419 |
| | | | | 123/703 |
| 8,631,786 | B2* | 1/2014 | Van Nieuwstadt | F01N 3/208 |
| | | | | 123/677 |
| 2001/0013245 | A1* | 8/2001 | Hanashiro | G01F 1/44 |
| | | | | 73/23.31 |
| 2003/0149536 | A1* | 8/2003 | Silvis | G01F 25/0053 |
| | | | | 702/24 |
| 2004/0231322 | A1* | 11/2004 | Miyahara | F01N 3/0807 |
| | | | | 60/277 |

(Continued)

FOREIGN PATENT DOCUMENTS

| EP | 1333270 A1 | 8/2003 |
| EP | 1936371 A1 | 6/2008 |

(Continued)

OTHER PUBLICATIONS

Office Action dated Dec. 6, 2016 issued for Japanese Patent Application No. 2013-073200, 3 pgs.

*Primary Examiner* — Peter Macchiarolo
*Assistant Examiner* — Hoang Nguyen
(74) *Attorney, Agent, or Firm* — Brooks Kushman P.C.

(57) ABSTRACT

The present invention is one that can, with suppressing moisture from condensing, easily set a dilution ratio to that enabling measurement accuracy to be improved, and provided with a constant volume sampling part that samples mixed gas that is controlled to have a constant flow rate, wherein the constant volume sampling part is provided with: a main flow path that is connected with an exhaust gas flow path and a diluent gas flow path, and intended to flow the mixed gas that is a mixture of exhaust gas and diluent gas; a constant flow rate mechanism that is configured to control a flow rate of the mixed gas to the constant flow rate; and a moisture detecting part that is provided on an upstream side of the constant flow rate mechanism to detect moisture in the mixed gas or the diluent gas.

4 Claims, 3 Drawing Sheets

(56) References Cited

U.S. PATENT DOCUMENTS

| | | | | |
|---|---|---|---|---|
| 2005/0252497 A1* | 11/2005 | Yasui | ........................ | G01K 7/42 |
| | | | | 123/697 |
| 2009/0000349 A1* | 1/2009 | Holt | .................... | G01N 1/2202 |
| | | | | 73/1.03 |
| 2010/0300180 A1* | 12/2010 | Bosi | ................... | G01N 33/0031 |
| | | | | 73/29.02 |

FOREIGN PATENT DOCUMENTS

| | | | |
|---|---|---|---|
| JP | 59-225332 A | | 12/1984 |
| JP | 06-341950 | | 12/1994 |
| JP | 08260844 | * | 1/1996 |
| JP | 10-019744 A | | 1/1998 |
| JP | 10-104134 | | 4/1998 |
| JP | 2000-292320 A | | 10/2000 |
| JP | 2005-055246 A | | 3/2005 |

* cited by examiner

EXHAUST GAS SAMPLING APPARATUS AND EXHAUST GAS SAMPLING METHOD

CROSS-REFERENCE TO RELATED APPLICATION

This application claims priority to JP Application No. 2013-073200, filed Mar. 29, 2013, the disclosure of which is incorporated in its entirety by reference herein.

TECHNICAL FIELD

The present invention relates to an exhaust gas sampling apparatus and an exhaust gas sampling method.

BACKGROUND ART

As a dilution sampling system that dilutes collected exhaust gas with diluent gas such as air to measure the concentration of a component contained in the exhaust gas, a constant volume dilution sampling apparatus (CVS) is widely used.

In the CVS, a critical flow rate of a critical flow venturi constituting a constant flow rate mechanism is set such that a ratio at which the exhaust gas is diluted with the diluent gas is increased to the extent of preventing moisture in the exhaust gas from condensing, for example, 10 to 20 times. On the other hand, in the case of increasing the dilution ratio, the concentration of the component contained in the diluted exhaust gas is decreased, and therefore measurement accuracy is deteriorated due to a measurement error.

For this reason, in the past, the critical flow rate of the critical flow venturi has been set so as to make the dilution ratio as small as possible to the extent of preventing the moisture in the exhaust gas from condensing. Specifically, on the basis of displacement, maximum vehicle speed (engine rotation speed), and the like of an engine (vehicle) as a test object, the critical flow rate of the critical flow venturi is set from user's intuition and empirical rule.

However, depending on the type of an engine (vehicle), a test condition, or the like, an amount of moisture contained in exhaust gas is different, and therefore as described above, in the case of setting the critical flow rate of the critical flow venturi on the basis of the user's intuition and empirical rule, there occurs a problem that the exhaust gas cannot be diluted to the extent of preventing the moisture in the exhaust gas from condensing, or the dilution ratio of the exhaust gas is excessively increased.

Also, in the case of using air as the diluent gas, an amount of moisture contained in the air causes an error, and as described above, in the case of setting the critical flow rate of the critical flow venturi on the basis of the user's intuition and empirical rule, there occurs a problem that the exhaust gas cannot be diluted to the extent of preventing the moisture in the exhaust gas from condensing, or the dilution ratio of the exhaust gas is excessively increased.

SUMMARY OF INVENTION

Technical Problem

Therefore, the present invention is mainly intended to make it possible to, with suppressing moisture from condensing, easily set a dilution ratio to that enabling measurement accuracy to be improved.

Solution to Problem

That is, an exhaust gas sampling apparatus according to the present invention is provided with a constant volume sampling part that samples mixed gas that is controlled to have a constant flow rate, wherein the constant volume sampling part is provided with: a main flow path that is connected with an exhaust gas flow path through which exhaust gas flows and a diluent gas flow path through which diluent gas flows, and intended to flow the mixed gas that is a mixture of the exhaust gas and the diluent gas; a constant flow rate mechanism that is provided in the main flow path, and configured to control a flow rate of the mixed gas flowing through the main flow path to the constant flow rate and enable the constant flow rate to be changed; a sampling flow path that is connected to the main flow path to sample the mixed gas that is controlled to have the constant flow rate; and a moisture detecting part that is provided on an upstream side of the constant flow rate mechanism to detect moisture in the mixed gas or the diluent gas.

Also, an exhaust gas sampling method using the exhaust gas sampling apparatus of the present invention is characterized by, on the basis of a moisture detected value obtained by the moisture detecting part, controlling the constant flow rate mechanism to adjust a dilution ratio of the exhaust gas.

If so, the present invention is configured to provide the moisture detecting part on the upstream side of the constant flow mechanism to detect an amount of the moisture in the mixed gas, so that the amount of the moisture contained in the mixed gas can be accurately grasped, and on the basis of the moisture amount, an optimum dilution ratio can be set. This makes it possible to suppress the moisture in the mixed gas from condensing, and prevent a reduction in measurement accuracy due to excessive dilution of the mixed gas to improve the measurement accuracy.

Also, in the case where an amount of moisture contained in the exhaust gas is preliminarily known, the important thing in setting the dilution ratio is an amount of the moisture contained in the diluent gas. In this case, the moisture detecting part is configured to detect the moisture in the diluent gas, so that by accurately grasping the moisture in the diluent gas, the moisture contained in the mixed gas can be accurately grasped, and therefore on the basis of an amount of the moisture, an optimum dilution ratio can be set. This makes it possible to suppress the moisture in the mixed gas from condensing, and prevent a reduction in measurement accuracy due to excessive dilution of the mixed gas to improve the measurement accuracy.

Desirably, the moisture detecting part detects relative humidity of the mixed gas or the diluent gas. By detecting the relative humidity as an amount of the moisture in the mixed gas or the dilution gas, a user can easily grasp the moisture amount because the relative humidity takes a value between 0% to 100%. Note that in the case where the moisture detecting part is one that detects absolute humidity or moisture concentration of the mixed gas or the dilution gas, it is difficult at a glance to see the value to set the dilution ratio.

Desirably, the exhaust gas sampling apparatus has a detected result display part that displays a detected result obtained by the moisture detecting part. If so, only by seeing a value in the detected result display part, an optimum dilution ratio can be set. Also, it can be easily determined whether or not a current dilution ratio is optimum.

Desirably, the constant flow rate mechanism is provided with: a plurality of critical flow venturis that respectively have different critical flow rates and are connected mutually in parallel; and a switching mechanism that switches to any one of the plurality of critical flow venturis to flow the mixed gas. If so, only by using the switching mechanism to switch among the critical flow venturis through which the mixed gas to flow, the dilution ratio can be easily changed.

Advantageous Effects of Invention

According to the present invention configured as described, on the upstream side of the constant flow rate mechanism, the moisture detecting part is provided, and therefore a dilution ratio can be easily set to that enabling measurement accuracy to be improved with moisture being suppressed from condensing.

DESCRIPTION OF EMBODIMENTS

In the following, an exhaust gas sampling apparatus according to the present invention is described with reference to the drawings.

An exhaust gas sampling apparatus 100 of the present embodiment is one that is used for a gas analyzing system for analyzing a component contained in exhaust gas emitted from, for example, an engine or the like, and employs a dilution sampling system that dilutes the exhaust gas with diluent gas such as air (diluent air) several times (e.g., 10 to 20 times) to measure concentration.

Figure 1:
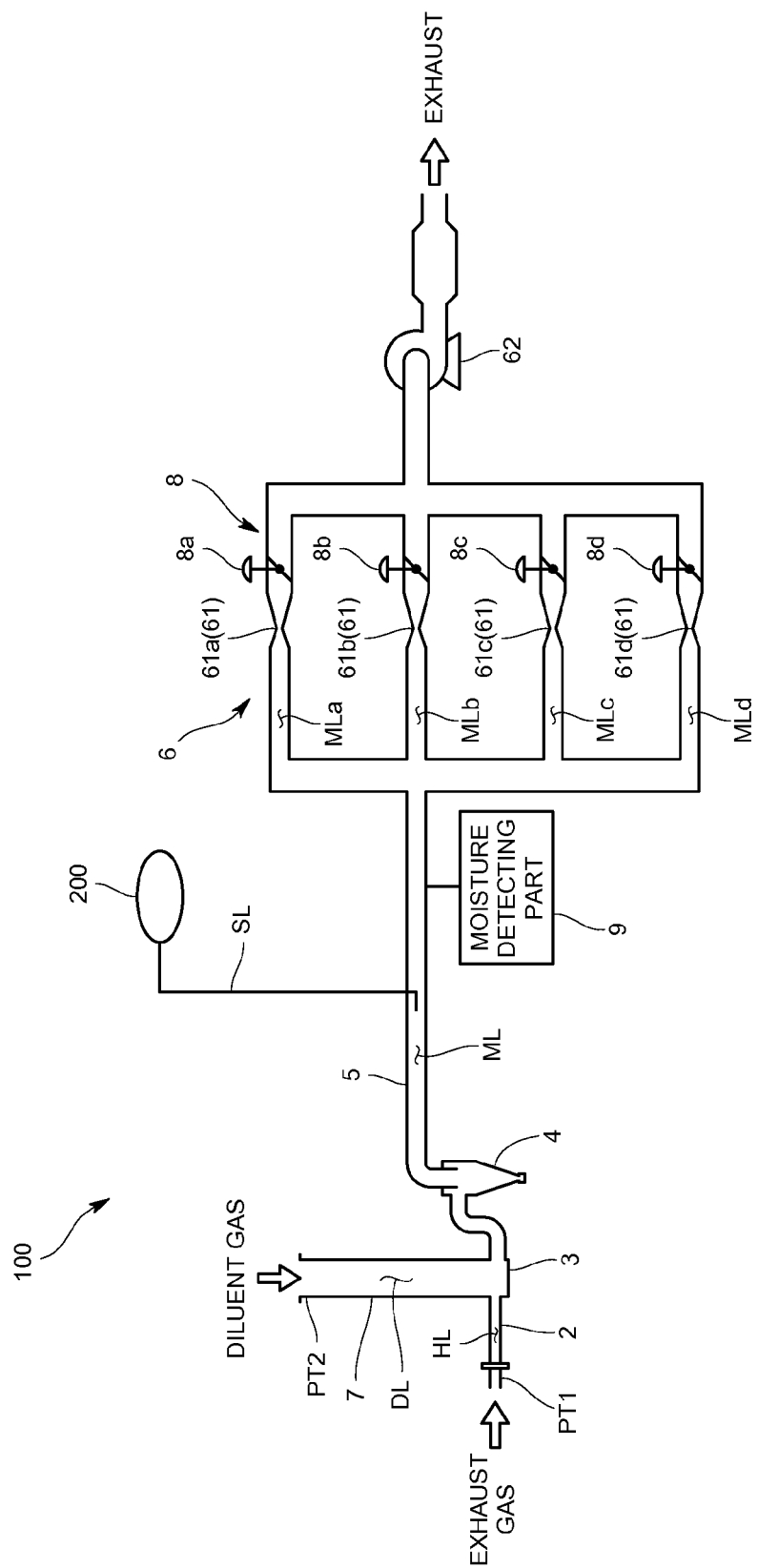
FIG. 1 is a schematic diagram illustrating a configuration of an exhaust gas sampling apparatus of the present embodiment.

Specifically, the exhaust gas sampling apparatus 100 is provided with a constant volume sampling part, and as illustrated in FIG. 1, provided with: an exhaust gas flow path HL of which one end is connected to an exhaust gas introduction port PT1 for introducing the exhaust gas; a diluent gas flow path DL of which one end is connected to a diluent gas introduction port PT2 for introducing the diluent gas; and a main flow path ML that is connected with the other end of the exhaust gas flow path HL and the other end of the diluent gas flow path DL, through which mixed gas (diluted exhaust gas) of the exhaust gas and the diluent gas flows.

The exhaust gas flow path HL is configured to include an exhaust gas introduction pipe 2 of which one end is provided with the exhaust gas introduction port PT1 to introduce the exhaust gas. The main flow path ML is configured to include: a mixing part 3 that is connected to the exhaust gas introduction pipe 2; a dust removing cyclone 4 that is connected downstream of the mixing part 3; a sampling pipe 5 that is connected downstream of the cyclone 4 and intended to sample the mixed gas that is controlled to have a constant flow rate as will be described later; and a constant flow rate mechanism 6 that is connected to the sampling pipe 5. Also, the diluent gas flow path DL is configured to include a diluent gas introduction pipe 7 of which one end is provided with the diluent gas introduction port PT2. In addition, the diluent gas introduction port PT2 is provided with a filter (not illustrated) for removing impurities in the air.

The mixing part 3 is one that is connected with the diluent gas introduction pipe 7 constituting the diluent gas flow path DL and the exhaust gas introduction pipe 2, and referred to as, for example, a mixing tee. Also, the sampling pipe 5 for performing constant volume sampling of the mixed gas is connected with a sampling flow path SL for collecting and introducing the diluted exhaust gas into an analyzing device 200 such as a gas collecting bag, PM collecting filter, or exhaust gas analyzing device.

The constant flow rate mechanism 6 is one that performs flow rate control so as to make a total flow rate of the exhaust gas introduced from the exhaust gas introduction pipe 2 and the diluent gas introduced from the diluent gas introduction pipe 7 equal to a constant flow rate, and can change the constant flow rate to thereby change a dilution ratio of the exhaust gas. The constant flow rate mechanism 6 in the present embodiment is configured to include: a main venturi 61 that is connected downstream of the sampling pipe 5 and includes a critical flow venturi (CFV); and a suction pump 62 that is connected downstream of the main venturi 61, such as a blower. The suction pump 62 makes a differential pressure between pressures on upstream and downstream sides of the main venturi 61 equal to or more than a required value to thereby make the total flow rate constant. In addition, the diluted exhaust gas sucked by the suction pump 62 is discharged outside.

Specifically, the constant flow rate mechanism 6 has a plurality of critical flow venturis 61a to 61d respectively having different critical flow rates, and the plurality of critical flow venturis 61a to 61d are connected mutually in parallel. That is, the main flow path ML is formed with branching into the plurality of critical flow venturis 61a to 61d, and the respective branched flow paths MLa to MLd are provided with the critical flow venturis 61a to 61d. The number of the plurality of critical flow venturis 61a to 61d in the present embodiment is four, and the critical flow rates of the critical flow venturis 61a to 61d are, for example, 5 [m2/min], 9 [m2/min], 15 [m2/min], and 20 [m2/min].

Also, in order to flow the mixed gas through at least one of the plurality of critical flow venturis 61a to 61d, the constant flow rate mechanism 6 has a switching mechanism 8 that switches among the critical flow rate venturis 61a to 61d through which the mixed gas is to flow. The switching mechanism 8 is configured to, in the respective branched flow paths ML1 to MLd, include on/off valves 8a to 8d provided on downstream sides of the critical flow venturis 61a to 61d, such as butterfly valves. The on/off valves 8a to 8d in the present embodiment are respectively subjected to manual on/off operations by a user.

Further, the exhaust gas sampling apparatus 100 of the present embodiment is, on an upstream side of the constant flow rate mechanism 6, provided with a moisture detecting part 9 that detects moisture in the mixed gas flowing through the main flow path ML.

The moisture detecting part 9 is provided on an upstream side of a branching point in the constant flow path mechanism 6 in the main flow path ML. In the present embodiment, the moisture detecting part 9 is provided on a downstream side of a sampling position of the sampling flow path SL. Note that the moisture detecting part 9 is only required to be located at a position enabling the moisture in the mixed gas to be detected, and specifically located at any position between a downstream side of the mixing part 3 and the upstream side of the constant flow rate mechanism 6 in the main flow path ML.

Also, the moisture detecting part 9 is a relative humidity sensor that detects relative humidity of the mixed gas flowing through the main flow path ML. Further, the relative humidity detected by the moisture detecting part 9 is displayed by a relative humidity display part (not illustrated) as a detected result display part so as to be visible by a user. In addition, the relative humidity display part may be provided on the moisture detecting part 9 itself, or configured as a display of a control device of the exhaust gas sampling apparatus 100; the relative humidity may be displayed on a display of the analyzing device 200 such as the exhaust gas analyzing device; or a display for displaying the relative humidity may be separately prepared.

An example of a dilution ratio setting method for the exhaust gas sampling apparatus 100 configured as described is described.

First, a user operates the on/off valves 8a to 8d of the switching mechanism 8 to enable the mixed gas to flow through the critical flow venturi 61d having the largest critical flow rate. In this state, the mixed gas is flowed to detect relative humidity of the mixed gas by the moisture detecting part 9. Note that by opening two or more of the on/off valves 8a to 8d, two or more critical flow venturis 61 may be combined to enable the mixed gas to flow.

Then, the user checks the relative humidity obtained by the moisture detecting part 9 to compare the relative humidity with a predetermined reference value (e.g., relative humidity of 85%). As a result of the comparison, to bring the relative humidity obtained by the moisture detecting part 9 close to the predetermined reference value, the user operates the switching mechanism 8 to decrease the dilution ratio, and attempts to achieve the maximum value to the extent not exceeding the predetermined reference value. After the adjustment of the dilution ratio, exhaust gas sampling measurement is started. As described, the dilution ratio is adjusted by gradually decreasing the dilution ratio from a large dilution ratio, and therefore the dilution ratio can be set with moisture being suppressed from condensing. Note that the dilution ratio may be set by gradually increasing the dilution ratio from a small dilution ratio.

The exhaust gas sampling apparatus 100 according to the present embodiment configured as described is configured to provide the moisture detecting part 9 on the upstream side of the constant flow rate mechanism 6, and detect the moisture in the mixed gas, so that the moisture contained in the mixed gas can be accurately grasped, and on the basis of an amount of the moisture, an optimum dilution ratio can be set. This enables measurement accuracy to be improved with the moisture in the mixed gas being suppressed from condensing.

Note that the present invention is not limited to the above-described embodiment.

Figure 2:
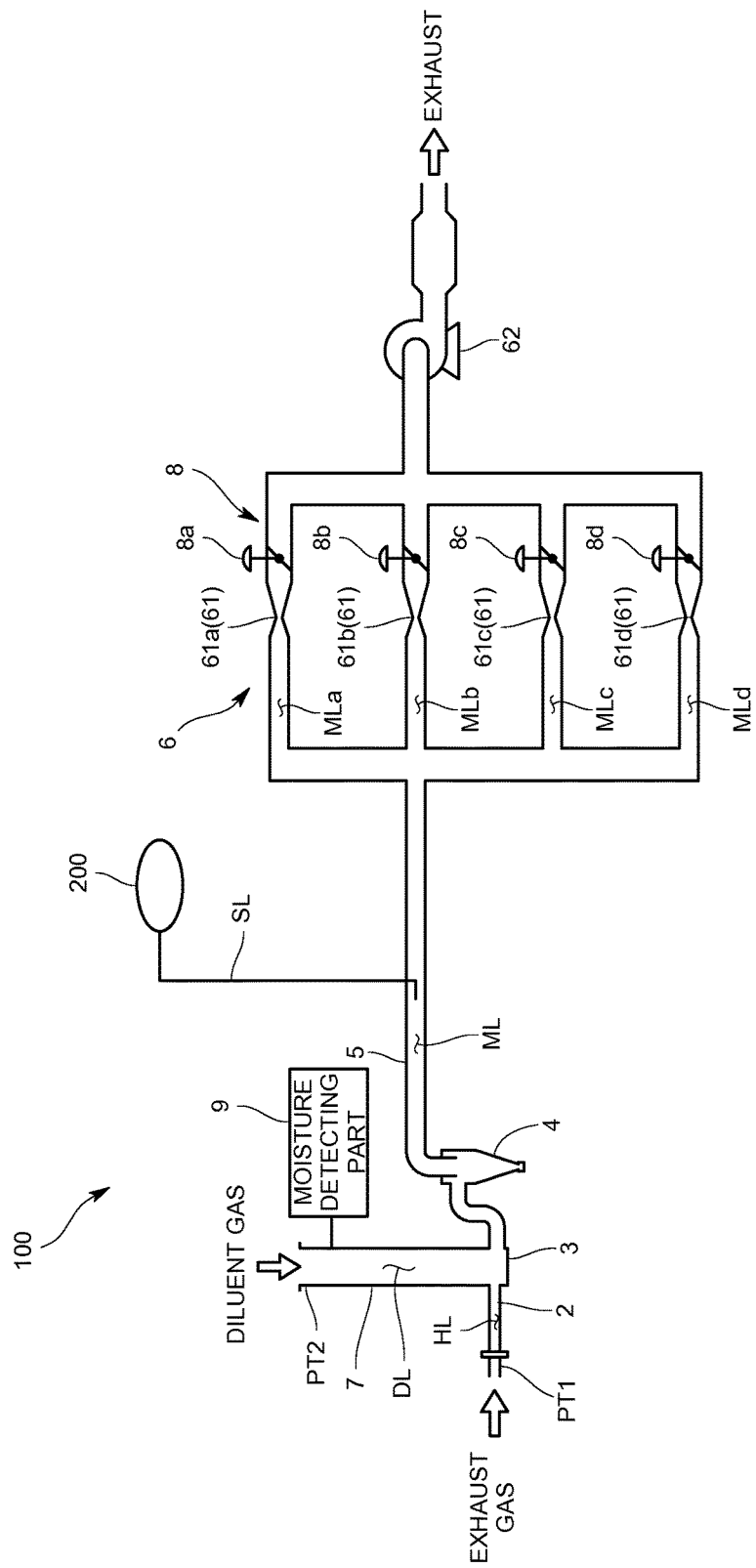
FIG. 2 is a schematic diagram illustrating a configuration of an exhaust gas sampling apparatus of a variation.

For example, in the above-described embodiment, the moisture detecting part 9 is provided in the main flow path ML to detect the moisture in the mixed gas; however, as illustrated in FIG. 2, the moisture detecting part 9 may be provided in the diluent gas flow path DL to detect moisture in the diluent gas. In the case where an amount of moisture contained in the exhaust gas is preliminarily known, an error component for determining the dilution ratio is caused by an amount of the moisture contained in the diluent gas, and therefore in the case of detecting the moisture in the diluent gas as described, the diluent ratio of the exhaust gas can be set to an optimum one in consideration of an influence of the error component. This enables measurement accuracy to be improved with the moisture in the mixed gas being suppressed from condensing. In addition, in this case, a moisture detecting part may be further provided in the exhaust gas introduction pipe 2 constituting the exhaust gas flow path HL.

Also, in the above-described embodiment, the dilution ratio is set with the mixed gas being flowed; however, as described above, the amount of the moisture contained in the diluent gas causes the error component, and therefore by flowing only the diluent gas, the moisture contained in the dilution gas may be detected to set the dilution ratio.

Further, the moisture detecting part 9 may be, in addition to one that detects the relative humidity, one that detects absolute humidity, or one that detects another value indicating a moisture amount, such as moisture concentration (volume fraction).

Still further, in the above-described embodiment, the air is collected from the diluent gas flow path DL, and used as the diluent gas; however, the exhaust gas sampling apparatus 100 may have a diluent air refining device to use diluent air produced by the diluent air refining device.

Figure 3:
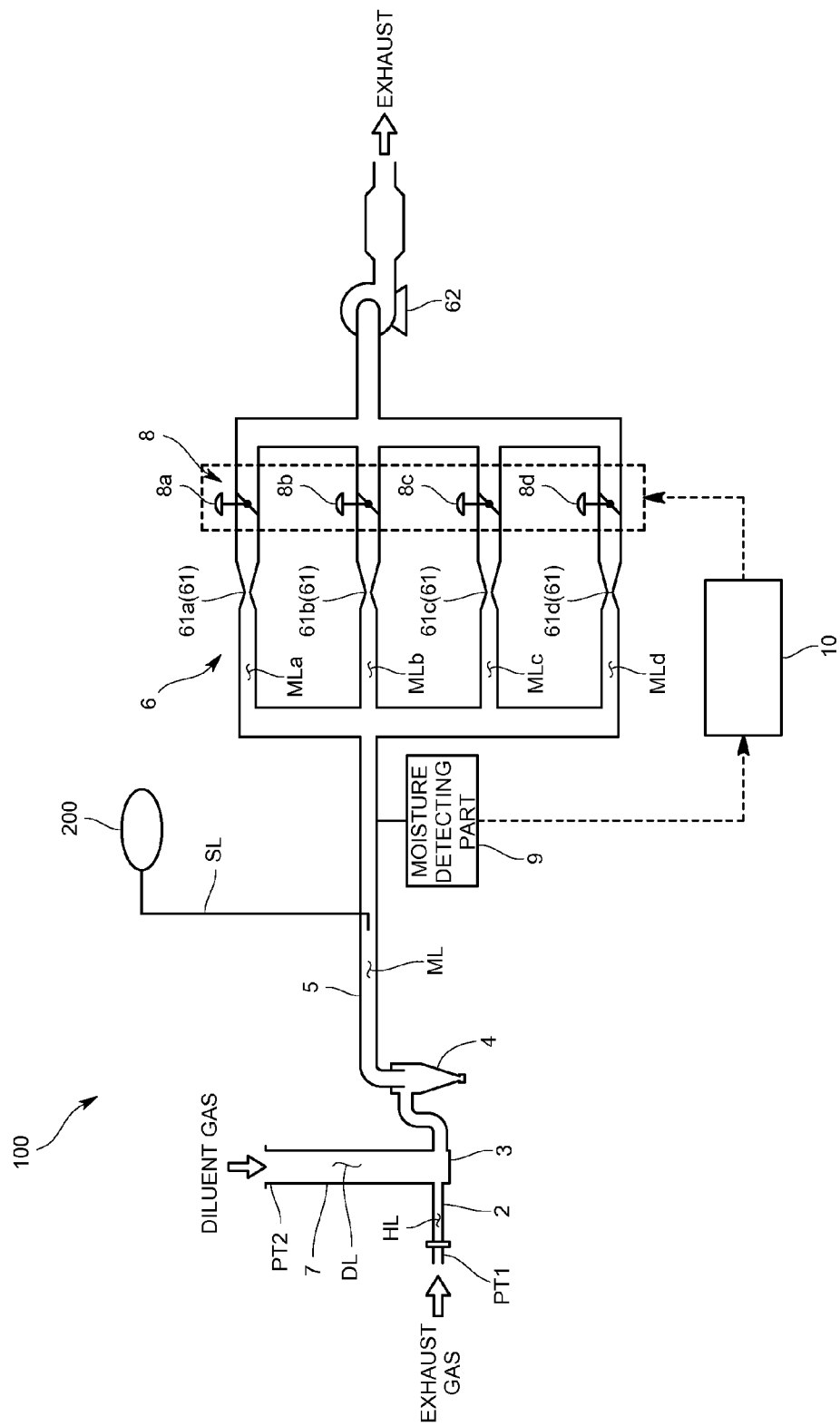
FIG. 3 is a schematic diagram illustrating a configuration of an exhaust gas sampling apparatus of another variation.

Yet further, in the above-described embodiment, the switching among the main venturis 61a to 61d is performed by the manual operations; however, the exhaust gas sampling apparatus 100 may automatically switch among the main venturis 61a to 61d. Specifically, as illustrated in FIG. 3, the on/off valves 8a to 8d serving as the switching mechanism 8 are respectively configured as solenoid valves, and a control device 10 performs on/off control of the on/off valves 8a to 8d. In this case, the control device 10 obtains a detection signal indicating a moisture amount such as relative humidity from the moisture detecting part 9, and compares the moisture amount indicated by the detection signal and a predetermined reference value with each other. Further, the control device 10 performs the on/off control of the on/off valves 8a to 8d to set the dilution ratio such that the amount of moisture contained in the mixed gas or the diluent gas takes a maximum value to the extent not exceeding the predetermined reference value.

In addition, the constant flow rate mechanism 6 in the above-described embodiment employs a multi-stage CVF system that has the plurality of critical flow venturis 61a to 61d, switches among the critical flow venturis through which the mixed gas is to flow, and thereby switches a flow rate of the mixed gas to a constant flow rate stepwise; however, the constant flow rate mechanism 6 may be the following one. For example, the constant flow rate mechanism may be one employing a venturi flowmeter system that uses a venturi as a flowmeter in a region before reaching a critical flow rate, and performs feedback control of a suction pump on a downstream side of the venturi to thereby perform continuous switching within a range not more than the critical flow rate of the venturi. Also, the constant flow rate mechanism 6 may be one employing a variable CFV system that mechanically changes a throat part area of a critical flow venturi to thereby continuously switch a gas flow rate. Further, the constant flow rate mechanism 6 may be one using, in addition to the critical flow venturi, a critical flow orifice (CFO). In addition, the constant flow rate mechanism 6 may be one employing a constant volume pump system not using the critical flow venturi.

Besides, it should be appreciated that the present invention is not limited to any of the above-described embodiment, but can be variously modified without departing from the scope thereof.

REFERENCE SIGNS LIST

100: Exhaust gas sampling apparatus
HL: Exhaust gas flow path
DL: Diluent gas flow path
ML: Main flow path
6: Constant flow rate mechanism
61a to 61d: Plurality of critical flow venturis
8: Switching mechanism
9: Moisture detecting part

What is claimed is:

1. An exhaust gas sampling method using an exhaust gas sampling apparatus, the exhaust gas sampling apparatus including a constant volume sampling part that is configured to sample mixed gas that is controlled to have a constant flow rate, wherein the constant volume sampling part comprises
- a main flow path that is connected with an exhaust gas flow path through which exhaust gas flows and a diluent gas flow path through which diluent gas flows, and intended to flow the mixed gas that is a mixture of the exhaust gas and the diluent gas,
- a constant flow rate mechanism that is provided in the main flow path, and configured to control a flow rate of the mixed gas flowing through the main flow path to the constant flow rate and enable the constant flow rate to be changed, wherein the constant flow rate mechanism includes a plurality of flow rate adjusting parts that respectively have different flow rates and are connected mutually in parallel, and a switching mechanism that switches to at least one of the plurality of flow rate adjusting parts to flow the mixed gas,
- a sampling flow path that is connected to the main flow path to sample the mixed gas that is controlled to have the constant flow rate, and
- a moisture detecting part that is provided on an upstream side of the constant flow rate mechanism to detect moisture in the mixed gas or the diluent gas, the method comprising:
- on a basis of a moisture detected value obtained by the moisture detecting part, operating the switching mechanism to switch to at least one of the plurality of flow rate adjusting parts to flow the mixed gas and to adjust a dilution ratio of the exhaust gas, wherein before an exhaust gas sampling measurement the dilution ratio is adjusted by gradually increasing or decreasing the dilution ratio to make the moisture detected value closer to a predetermined reference value, and after the adjustment of the dilution ratio, the exhaust gas sampling measurement is started.

2. The exhaust gas sampling method according to claim 1, wherein the moisture detecting part is configured to detect relative humidity of the mixed gas or the diluent gas.

3. The exhaust gas sampling method according to claim 1, wherein the exhaust gas sampling apparatus further includes a detected result display part that is configured to display a detected result obtained by the moisture detecting part.

4. An exhaust gas sampling apparatus comprising: a constant volume sampling part that is configured to sample mixed gas that is controlled to have a constant flow rate, wherein the constant volume sampling part includes
- a main flow path that is connected with an exhaust gas flow path through which exhaust gas flows and a diluent gas flow path through which diluent gas flows, and intended to flow the mixed gas that is a mixture of the exhaust gas and the diluent gas,
- a constant flow rate mechanism that is provided in the main flow path, and configured to control a flow rate of the mixed gas flowing through the main flow path to the constant flow rate and enable the constant flow rate to be changed, wherein the constant flow rate mechanism includes a plurality of flow rate adjusting parts that respectively have different flow rates and are connected mutually in parallel, and a switching mechanism that switches to at least one of the plurality of flow rate adjusting parts to flow the mixed gas,
- a sampling flow path that is connected to the main flow path to sample the mixed gas that is controlled to have the constant flow rate, and
- a moisture detecting part that is provided on an upstream side of the constant flow rate mechanism to detect moisture in the mixed gas or the diluent gas; and
- a control device that is configured to automatically switch the switching mechanism on a basis of a moisture detected value obtained by the moisture detecting part to adjust a dilution ratio of the exhaust gas, wherein before an exhaust gas sampling measurement, the control device switches the switching mechanism to adjust the dilution ratio by gradually increasing or decreasing the dilution ratio to make the moisture detected value closer to a predetermined reference value, and the exhaust gas sampling apparatus starts the exhaust gas sampling measurement.

* * * * *